(12) United States Patent
Buerger

(10) Patent No.: US 10,527,215 B2
(45) Date of Patent: Jan. 7, 2020

(54) ADAPTER HOUSING AND CONNECTING DEVICE FOR CHROMATOGRAPHY

(71) Applicant: DIONEX SOFTRON GMBH, Germering (DE)

(72) Inventor: Daniel Buerger, Raisting (DE)

(73) Assignee: Dionex Softron GMBH, Germering (DE)

( * ) Notice: Subject to any disclaimer, the term of this patent is extended or adjusted under 35 U.S.C. 154(b) by 0 days.

(21) Appl. No.: 14/592,681

(22) Filed: Jan. 8, 2015

(65) Prior Publication Data

US 2015/0198567 A1    Jul. 16, 2015

(30) Foreign Application Priority Data

Jan. 15, 2014   (DE) .................. 10 2014 100 430

(51) Int. Cl.
*B01D 15/12*   (2006.01)
*F16L 21/035*  (2006.01)
(Continued)

(52) U.S. Cl.
CPC ............ *F16L 55/00* (2013.01); *B01D 15/125* (2013.01); *F16L 21/035* (2013.01); *F16L 21/04* (2013.01); *G01N 30/14* (2013.01); *G01N 30/461* (2013.01); *G01N 30/6004* (2013.01); *G01N 30/6026* (2013.01); *G01N 30/6039* (2013.01); *G01N 30/6091* (2013.01); *G01N 2030/027* (2013.01); *G01N 2030/085* (2013.01); *G01N 2030/143* (2013.01)

(58) Field of Classification Search
CPC .. G01N 30/46; G01N 30/465; G01N 30/6026; G01N 30/6039; G01N 30/6091; G01N 30/6004; G01N 30/6073; G01N 30/14; G01N 30/461; G01N 2030/027; G01N 2030/085; G01N 2030/143; F16L 21/03; F16L 21/035; F16L 21/04; F16L 55/00; F16L 2201/40; F16L 9/14; F16L 9/147; F16L 58/10; F16L 19/041; F16L 37/02; F16L 25/0018; B01D 15/22; B01D 15/125
See application file for complete search history.

(56) References Cited

U.S. PATENT DOCUMENTS 4,281,679 A  *  8/1981  Stearns .................. F16K 15/04
                                                    137/515.5
4,690,437 A  *  9/1987  Anderson, Jr. .... G01N 30/6026
                                                    285/339
(Continued)

FOREIGN PATENT DOCUMENTS

DE       3115873 A1    1/1982
DE      69417240 T2    7/1999
(Continued)

*Primary Examiner* — Benjamin L Lebron

(57) ABSTRACT

An adapter housing is described that can be used for high performance liquid chromatography, which can be releasably connected to a socket unit. The adapter housing includes a bore which passes through the adapter housing and a pre-column which can be arranged in the bore to protect the separation column from contaminants and/or to concentrate the fluid to be analyzed. A sealing element seals the adapter housing in relation to the socket unit at the end-face wall of a pilot bore.

13 Claims, 4 Drawing Sheets

(51) Int. Cl.
*F16L 21/04* (2006.01)
*F16L 55/00* (2006.01)
*G01N 30/14* (2006.01)
*G01N 30/46* (2006.01)
*G01N 30/60* (2006.01)
*G01N 30/02* (2006.01)
*G01N 30/08* (2006.01)

(56) References Cited

U.S. PATENT DOCUMENTS

| | | | | |
|---|---|---|---|---|
| 4,806,238 A | * | 2/1989 | Sattler | G01N 30/6039 210/198.2 |
| 5,227,059 A | * | 7/1993 | Shepherd | G01N 30/6004 210/198.2 |
| 5,525,303 A | * | 6/1996 | Ford | B01D 15/125 210/198.2 |
| 5,863,428 A | * | 1/1999 | Ma | B01D 15/22 210/198.2 |
| 5,911,954 A | | 6/1999 | Ford et al. | |
| 6,162,362 A | | 12/2000 | Ma et al. | |
| 6,679,989 B2 | * | 1/2004 | Willis | G01N 30/08 210/198.2 |
| 7,132,046 B2 | * | 11/2006 | Cheong | B01D 15/22 210/198.2 |
| 2008/0237112 A1 | * | 10/2008 | Ford | G01N 30/6039 210/232 |
| 2010/0213112 A1 | | 8/2010 | Bischoff et al. | |
| 2012/0024411 A1 | * | 2/2012 | Hahn | B01D 15/22 138/109 |
| 2012/0061955 A1 | * | 3/2012 | Hochgraeber | G01N 30/6026 285/342 |

FOREIGN PATENT DOCUMENTS

| | | | |
|---|---|---|---|
| DE | 299104090 U1 | 9/2000 | |
| DE | 69715437 T2 | 10/2003 | |
| DE | 202006020473 U1 | 10/2008 | |
| WO | WO 2010133192 A1 * | 11/2010 | G01N 30/6026 |

\* cited by examiner

ADAPTER HOUSING AND CONNECTING DEVICE FOR CHROMATOGRAPHY

CROSS REFERENCE TO RELATED APPLICATIONS

This application claims the priority benefit under 35 U.S.C. § 119 to German Patent Application No. 10 2014 100 430.2 by inventor Daniel Buerger for "Adapter Housing," filed on Jan. 15, 2014, the disclosure of which is incorporated herein by reference.

FIELD OF THE INVENTION

The present invention relates to an adapter housing for receiving a component to be traversed, in particular for high performance liquid chromatography (HPLC), as well as to a connecting device which includes an adapter housing.

BACKGROUND

The separation columns used in the area of chromatography, for example high performance liquid chromatography (HPLC), gas chromatography (GC), supercritical fluid chromatography (SFC) and capillary electro-chromatography (CEC), in many cases include very valuable packing material which should be protected against contaminants which can be absorbed in the packing material. These types of contaminants impair the separation accuracy of the separation column. However, the contaminants are very frequently contained in the fluid to be analyzed and cannot be removed in many cases by pure filtration. The use of a pre-column can provide a remedy in this connection. A pre-column is arranged upstream of the actual separation column and can include the same packing material as the separation column, however in many cases in smaller volumes. As a result, on the one hand the fluid to be analyzed is filtered and on the other hand it can also be concentrated.

Separation columns with a pre-column are described, for example, in DE 694 17 240 T2 and in DE 697 15 437 T2. The fluid to be analyzed is guided via capillary tubes to the columns, the capillary tubes being connected to the respective columns by way of connecting devices, frequently designated as fittings. In DE 694 17 240 T2, the pre-column is arranged in an adapter housing which is screwed into a socket unit of the connecting device so that no further capillary tube is required, as is the case, for example, in DE 31 15 873 A1.

Generally to be observed is a tendency toward packing materials with ever decreasing particle sizes, as a result of which the available surface-volume ratio is enlarged, which, in turn, increases the separation accuracy. However, as a result pressure loss in the separation column and the pre-column increases, as a result of which ever increasing pressures are required so that the fluid to be analyzed is able to run through the separation column and the pre-column. In this case, the sealing of the capillary tube in the region of the fittings poses a particular problem. In many cases the fittings comprise a so-called cutting ring screw connection which consists of a cap nut, a clamping cone and a cutting ring. The capillary tubes are pushed into a pilot bore of the fittings. As a result of tightening the cap nut, which tapers conically inward, the cutting ring is compressed, as a result of which its wedge-shaped ring inside cuts into the wall of the capillary tube and produces a tight positive locking connection. Due to its design, in this connection the outside diameter of the capillary tubes has to be somewhat smaller than the diameter of the pilot bore such that a small gap is formed here. When viewed from the end of the capillary tube which is pushed into the pilot bore, the clamping core is situated somewhat set back such that a certain dead volume is produced around the end of the capillary tube, which results in the fluid to be analyzed being carried over which has a negative effect on the separation accuracy of the columns. In addition, the fluid to be analyzed can still be contaminated by the fluid analyzed beforehand.

The problem of the dead space of the cutting ring screw connection is made even worse as a result of all the components having to be matched to one another. No cutting ring screw connections can be used for fittings with different pilot bore lengths without increasing the dead space further.

SUMMARY

The disadvantages connected to the dead space occur both in the case of the separation columns and in the case of the pre-columns. It is the object of the present invention to develop an adapter housing of the type mentioned in the introduction, with which, for example, a pre-column can be connected upstream of a separation column with a minimized dead volume.

The adapter housing according to the invention can be inserted or screw-connected into a socket unit. The socket unit can be part of a separation column apparatus or can also provide an independent coupling element, to which inlet and outlet pipe elements or capillary tubes can be connected. In particular, the socket unit serves for the purpose of incorporating a pre-column into the flow path of a fluid to be analyzed upstream of the separating column.

The adapter housing includes a sealing element which can be inserted into the adapter housing and which seals the adapter housing in relation to the socket unit on the end-face wall of the pilot bore when the adapter housing is introduced into the receiving opening of the socket unit. Unlike the cutting ring screw connections, according to the invention the adapter housing is sealed in relation to the socket unit on the end-face wall of the pilot bore such that the force necessary for surface pressure acts in an axial manner. A socket capillary tube extends away from the end-face wall of the pilot bore and can serve, in particular, for the purpose of guiding the fluid to be analyzed, which has been introduced from a capillary tube into the pre-column, further to a separation column. The socket capillary tube can lead directly into the separation column for this purpose. As an alternative to this, the socket capillary tube could also lead to a further pilot bore of the socket unit, into which a suitable connector unit can be inserted, through which the fluid is able to be forwarded. In this case, the socket unit could be realized in an extensively or completely symmetrical manner with respect to a plane of symmetry perpendicular to the socket capillary tube.

As a result of sealing at the end-face wall, sealing is already effected in the direct vicinity of the socket capillary tube such that the fluid to be analyzed can in no way reach the radial wall first, as a result of which the dead space is clearly reduced. As a consequence, the outside diameter of the part of the adapter housing which is introduced into the pilot bore can be chosen more freely. Even if choosing the outside diameter substantially equal to the diameter of the pilot bore is preferred, the outside diameter can be chosen to be smaller within certain limits, as a result of which tolerance requirements and expenditure on production are decreased, which reduces production costs. A certain plastic deformability of the sealing element can additionally result in the transition from the adapter housing into the socket unit being sealed in an axial and radial manner by the sealing element fitting snugly against the end face of the socket unit and against the inside wall of the receiving opening of the socket unit. To this end, the sealing element can comprise a somewhat larger outer diameter than the pilot bore. When mounting the adapter housing in the socket unit, as a result of pressure being applied to the adapter housing the sealing element is deformed elastically or plastically and consequently fills out the front region of the pilot bore in the socket unit in an optimum manner toward the end face and toward the wall face of the pilot bore. As a result, an optimum sealing effect is produced in this region. The risk of leakage and of realizing dead spaces is reduced.

In addition, the sealing in the region of the end face and of the radial lateral surface of the socket unit prevents direct contact between the fluid to be analyzed and the, as a rule, metal socket unit such that the fluid is able to be guided in a bio-inert manner.

As a result of the sealing element abutting against the end-face wall of the pilot bore in the mounted state, the sealing element also functions as a stop such that no specific bore lengths are fixed, as a result of which the adapter housing according to the invention is able to be used in fittings with different pilot bore lengths.

In the case of cutting ring screw connections, the sealing action is obtained by a high degree of surface pressure which acts radially on the capillary tube and which can result in plastic deformation, which makes repeated use of the adapter housing difficult or even rules it out altogether. Only the sealing element, which can be exchanged relatively easily, is deformed according to the invention, whereas on account of the axial sealing the adapter housing is not deformed plastically and consequently is able to be re-used multiple times. The surface pressure necessary for sealing is determined exclusively as a result of how far the adapter housing is screwed into the socket unit, which is why the adapter housing can also be used in socket units with different pilot bore lengths. High pressures are able to be sealed in a reliable manner without the adapter housing having to be screwed into the socket unit using a tool, as a result of which the connecting device is easy to mount.

According to the invention, the sealing element comprises a first sealing portion and second sealing portion which adjoins thereto preferably in an integral manner. The first sealing portion, in this case, abuts against the front end of the adapter housing outside of said adapter housing, where it brings about the sealing in relation to the socket unit (see above). The second sealing portion can be inserted into the bore of the adapter housing such that the lateral surface of the pre-column is surrounded by the second sealing portion along its longitudinal extension. In this case, it has a substantially hollow-cylindrical form and surrounds the cavity with an inner diameter in which the pre-column can be arranged. As a result of the insertable development of the sealing element, a unit of the seal with the pre-column located inside, realized as a cartridge, can be exchanged in an easier manner. On the other hand, there is the particular advantage of the seal assuming a dual function by not only sealing in relation to the socket unit at the first sealing portion, preferably as a result of deforming, but at the same time lining the fluid in the pre-column along its lateral surface and thus protecting it against unwanted contact with the adapter housing. The seal can be realized and formed for this purpose such that it surrounds the fluid in a bio-inert manner along its entire flow path prior to entry into until exit from the pre-column such that it does not experience any unwanted reaction or modification from contact with the material of the adapter housing.

On the other hand the sealing element not only seals the adapter housing in relation to the socket unit by way of its front portion, but by way of its second portion it also seals the pre-column itself such that no further measures have to be taken for sealing the pre-column, as a result of which the design of the adapter housing is simplified. The sealing element preferably extends over the entire length of the pre-column such that the lateral surface thereof is fully sealed in a bio-inert manner against unwanted contact between the fluid and, for example, metal.

The second sealing portion of the adapter housing seals in relation to the socket unit at the radial wall and at the end-face wall, for which purpose the first sealing portion, prior to being inserted, can also comprise a slightly larger outside diameter than the pilot bore. As a result, the necessary surface pressure can be adjusted in order to be able to seal the adapter housing reliably in a radial and axial manner in relation to the socket unit even at high pressures.

In an expedient manner, the sealing element includes a through-bore for receiving the pre-column which extends coaxially with respect to the socket capillary tube. At one rear end of the second sealing portion which is remote from the socket unit, the sealing element can preferably be realized in the region of a third sealing portion with an enlarged outside diameter which engages as an undercut into the bore of the adapter housing, which is realized in a complementary manner for this purpose in order to secure the sealing element axially at the front against slipping out. At its front, first portion, the sealing element can comprise an end diameter which is reduced in relation to the bore of the adapter housing in order to form, as a result, an end face or an axial stop for a restraining device (for example filter) by way of which the particles of the packing material of the pre-column are restrained and are prevented from being transported away by the fluid to be analyzed.

In a preferred development, at the rear end of the sealing element which is remote from the socket unit a closure can be introduced into the bore of the adapter housing for closing the pre-column, wherein the closure comprises a central through-channel for directing the fluid to be analyzed to the pre-column. The closure keeps forces, which are introduced into the adapter housing from the capillary tube or from a socket unit guiding the capillary tube, away from the pre-column, as a result of which it is protected. In addition, the closure fixes the pre-column in the desired position.

The sealing element can be connected to the adapter housing in a different manner. As a result of crimping, that is pressure turned radially inward being applied locally onto the tubular wall of the adapter housing which includes the sealing element, said adapter housing is deformed inward, as a result of which a strong frictional locking connection and/or positive locking connection to the sealing element is produced. The radial expansion of a rear, third sealing portion, which projects rearward beyond the bore of the adapter housing, also produces a positive locking stop which prevents the sealing element from being pulled out forward. Finally, a comparable expansion of the seal on the front, first sealing portion also undercuts the wall of the bore of the adapter housing which connects rearward thereto such that the sealing element is also prevented from being pushed further into the bore.

Also conceivable is a type of cartridge structure where the pre-column plus sealing element is arranged outside the adapter housing in a sleeve which, in turn, can then be inserted into the adapter housing, which possibly simplifies assembly. The sleeve can also be crimped in order to connect the seal to the pre-column in a reliable manner. The cartridge can be secured in the adapter housing against displacement by means of a suitable, releasable or non-releasable fastening, for example expanding the seal in an end region (third sealing portion) followed by clamping of the expanded region by means of a closure.

In addition to or as an alternative to a filter which is arranged at the front end of the pre-column, a filter for filtering the fluid to be analyzed and for restraining the pre-column packing can also be provided which, in the mounted state, abuts against the closure at the rear end of the column or of the sealing element. The fluid to be analyzed is filtered through the further filter before it reaches the pre-column such that contamination of the pre-column is reduced and its service life increased. In addition, the further filter fixes the packing material of the pre-column such that particles of the packing material are not able to migrate in an uncontrolled manner. The further filter can also be developed as fritte. Alternatively or additionally, a filter can also be provided in instead of on the closure. Along with the above-mentioned advantages of a filter, assembly in said development is particularly simple as the filter is arranged in the closure and consequently does not have to be separately positioned.

A further aspect of the present invention relates to a connecting device for connecting components which are to be traversed, in particular from high performance liquid chromatography (HPLC), said connecting device having an adapter housing of the afore-described type. The connecting device further includes a socket unit of the type also described above which can be directly part of a separation column or can be an independent component. In addition, the connecting device preferably includes a connector housing to which, for example, a capillary tube for supplying a fluid to be analyzed can be connected by the connector housing being releasably fastenable to a connecting portion of a bore which passes through the adapter housing. Instead of directly connecting a separation column by means of a socket unit that is associated with the column, the separation column can also be connected to the connecting device by means of such a connector housing.

The technical effects and advantages that can be achieved using the connecting device according to the invention correspond to those which have been discussed for the adapter housing according to the invention. It is to be mentioned in particular that it is possible in a simple manner using the connecting device according to the invention to connect a pre-column upstream of a separation column without disruptive dead spaces being created.

BRIEF DESCRIPTION OF THE DRAWINGS

The present invention is described in detail below by way of preferred exemplary embodiments with reference to the accompanying drawings, in which, in each case by way of a sectional representation.

DETAILED DESCRIPTION OF EMBODIMENTS

Figure 1:
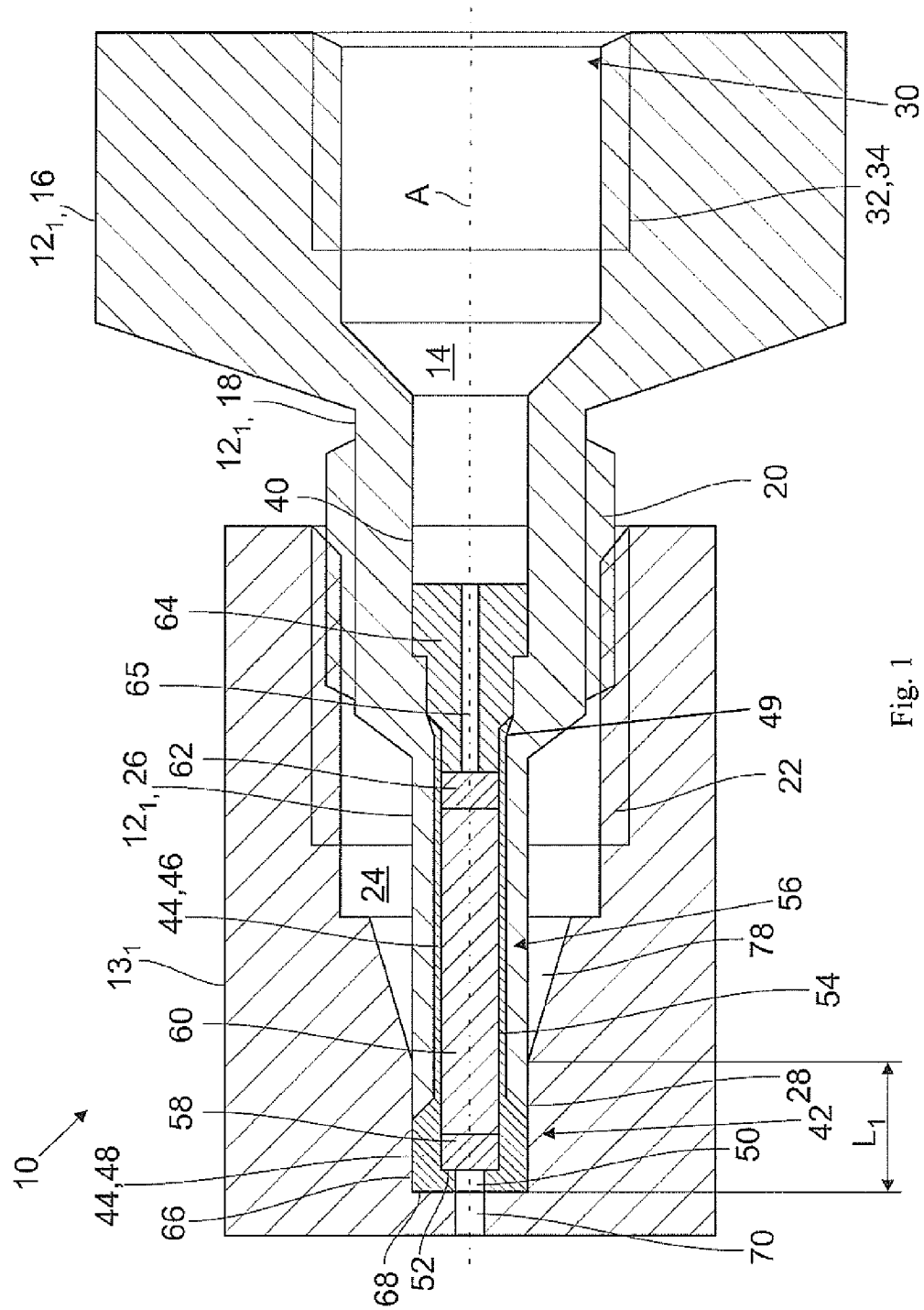
FIG. 1 shows a connecting device according to the invention with an adapter housing according to a first embodiment which is screwed into a first socket unit.

FIG. 1 shows a connecting device 10 according to the invention which includes a first embodiment of an adapter housing $12_1$ according to the invention as well as a first socket unit $13_1$. The adapter housing $12_1$ comprises a bore 14 which penetrates the adapter housing $12_1$ completely. The adapter housing $12_1$ comprises a first portion 16 with a first outside diameter at which the adapter housing $12_1$ is able to be grasped and moved, in particular rotated, by a user. In addition, the adapter housing $12_1$ comprises a second portion 18 with a second outside diameter on which is arranged an external thread 20 by way of which the adapter housing $12_1$ is able to be screwed into an internal thread 22, which is arranged in a receiving opening 24 of the socket unit $13_1$. Over and above this, the adapter housing $12_1$ comprises a third portion 26 with a third outside diameter which corresponds approximately to the diameter of a pilot bore 28 which is arranged in the socket unit $13_1$. The pilot bore 28 has a length $L_1$. The first outside diameter is the largest, whilst the third outside diameter is the smallest of the outside diameters of the adapter housing $12_1$. The adapter housing $12_1$ can be produced, for example, from metal or ceramic.

In the first portion 16, the bore 14 of the adapter housing $12_1$ comprises a first opening 30 with a first inside diameter which corresponds approximately to the second outside diameter of the second portion 18.

Figure 2:
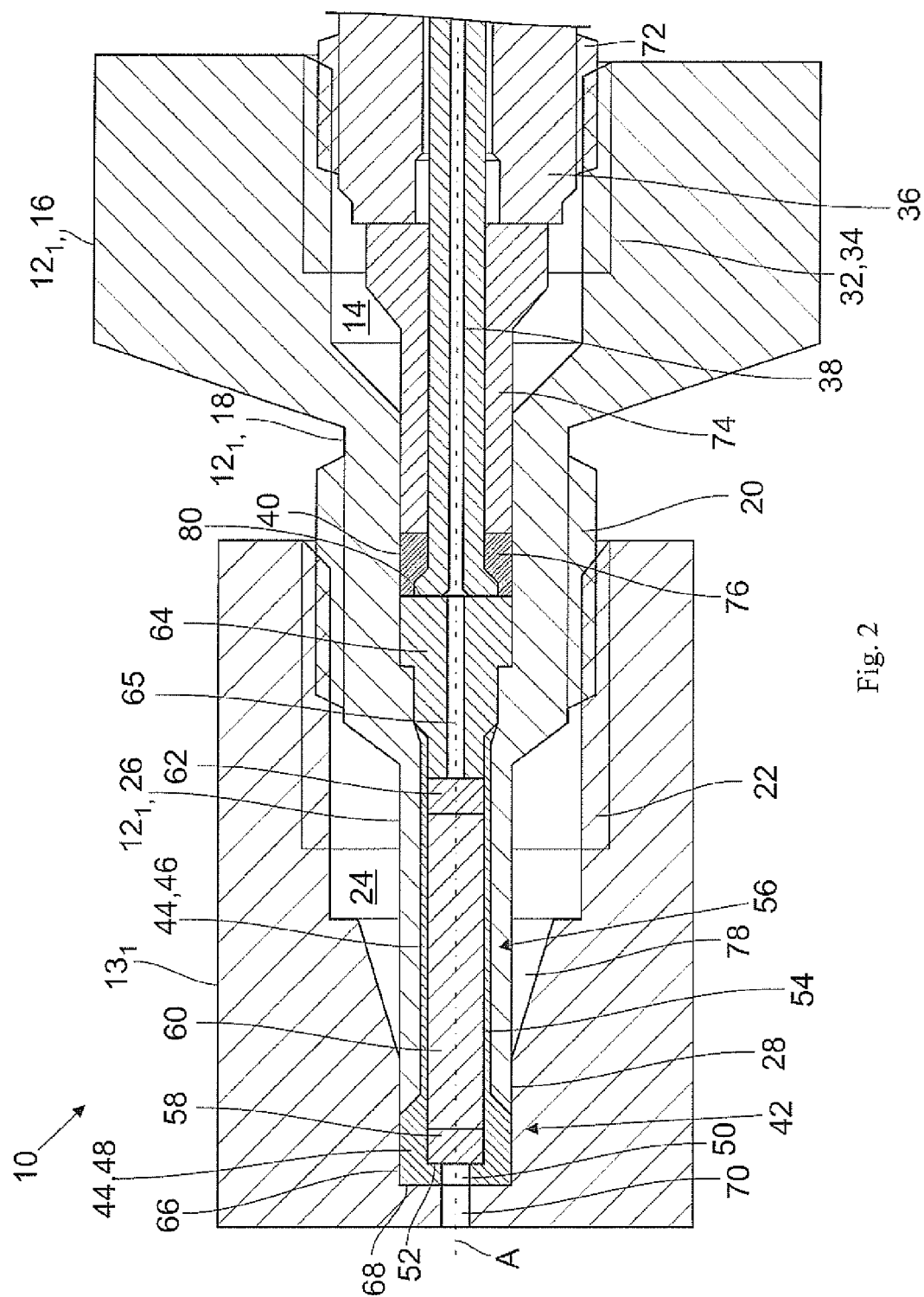
FIG. 2 shows the connecting device according to the invention shown in FIG. 1, wherein a capillary tube is connected to the adapter housing.

Arranged in the first portion 16 is a connecting portion 32, which includes an internal thread 34, into which can be screwed a connector housing 36 (cg. FIG. 2), in which is arranged a capillary tube 38 in which the fluid to be analyzed is guided. In the region of the second portion 18, the bore 14 comprises a second inside diameter which is smaller than the first inside diameter, the bore 14 tapering conically from the first to the second inside diameter. In the region of the second inside diameter, the bore 14 comprises a particularly precisely produced fitting portion 40 which is produced with tighter production tolerance. The bore 14 then tapers in a step-shaped manner to a third inside diameter in order then to reduce in a conical manner to a fourth inside diameter. At its front end which is remote from the first portion 16, the bore 14 passes from the fourth inside diameter in a funnel-shaped manner over into the third outside diameter and forms a second opening 42.

An elongated sealing element 44 is inserted by means of the second opening 42 into the bore 14 of the adapter housing $12_1$ which comprises a first sealing portion 48 and a second sealing portion 46. The second sealing portion 46 has a substantially hollow-cylindrical form and surrounds a cavity which can be filled out by a pre-column. The second sealing portion 46 comprises an outside diameter which corresponds substantially to the fourth inside diameter of the bore 14 of the adapter housing $12_1$. The sealing element 44 can be reshaped and expanded at a third sealing portion 49 at the free rear end of the second sealing portion 46 using a corresponding tool such that it is fixed, for example as a result of clamping by means of a closure (see below), at a stop region of the adapter housing, in particular at the conical transition of the bore 14 from the third to the fourth inside diameter. As a result, the fluid can also be isolated in a contact-tight (bio-inert) manner in relation to the adapter housing in the region of the rear end of the pre-column. In addition, the sealing element can easily be fixed on the adapter housing in this manner.

At the front end, the second sealing portion 46 expands conically onto the first sealing portion 48, where it corresponds with the form of the opening 42. The outside diameter of the first sealing portion 48, in this case, can be chosen to be somewhat larger than the fourth inside diameter of the adapter housing $12_1$, and can even be slightly larger than the third outside diameter of the adapter housing $12_1$ such that the first sealing portion 48 projects radially somewhat beyond the third portion 26 of the adapter housing $12_1$. In addition, the first sealing portion 48 also projects axially somewhat beyond the front end of the adapter housing $12_1$.

In the first sealing portion 48, the sealing element 44 comprises a through-bore 50 with a diameter which is somewhat smaller than the diameter of the cavity such that an end face 52 is formed. A pre-column 56 is inserted into the cavity. It includes a filter 58 which touches the end face 52. Arranged adjoining the rear side of the filter is a pre-column packing 60 which abuts against a further filter 62 by way of its rear end. Said filter 62, and with it the entire pre-column, is fixed by a closure 64 which comprises a through-channel 65 for the fluid to be analyzed to pass through. The sealing element 44 can be produced from a plastics material such as polyetheretherketone (PEEK). It is possible, in particular, to use biocompatible materials.

The third portion 26 of the adapter housing $12_1$ can be introduced into the pilot bore 28 of the socket unit $13_1$ which, in the example shown, passes over into the expanded receiving opening 24 via a conical transition region 78. The pilot bore 28 comprises a radial wall 66 and an end-face wall 68. A socket capillary tube 70, by means of which the fluid to be analyzed is guided to a separation column (not shown), connects to the end-face wall 68 axially and concentrically with respect to the axis of the pre-column 56. (Not shown is a realization variant of the socket unit where a comparable further receiving opening is provided in the housing of the socket unit on the end of the socket capillary tube 70 which is remote from the receiving opening 24. The separation column or another HPLC component could be connected here by means of a connector unit instead of realizing the socket unit integrally with or at any rate as part of the separation column.)

In order to be able to use the adapter housing $12_1$ in a functional manner, the sealing element 44 is initially inserted by means of the second opening 42 into the bore 14 of the adapter housing $12_1$. If the sealing element 44 is produced from a suitable plastics material, it can also be injected directly into the bore 14. Using a corresponding tool, the sealing element 44 is deformed at its free rear end such that it abuts against the conical transition from the third into the fourth inside diameter of the bore 14, as a result of which the position of the sealing element is fixed. The filter 58, the pre-column packing 60 and the further filter 62 are then introduced into the sealing element 44 by means of the first opening and closed by way of the closure 64. The position of the closure 64 is fixed by the inside diameter of the bore 14 which reduces in a step-like manner such that the pre-column packing 60 is not able to be compressed too strongly.

In addition, the closure 64 can be clamped, for example by means of an intermediate part which acts in a rearward manner and thus, depending on production dimensions and tolerances, can determine, in a targeted manner, the packing density of the pre-column packing and remove air out of the pre-column. As the position of the closure 64 is fixed, the sealing element 44 and the pre-column 56 are also consequently correctly positioned such that faulty installation is as good as impossible.

The adapter housing $12_1$ is then connected to the socket unit $13_1$, to which end the adapter housing $12_1$ is introduced into the receiving opening 24 of the socket unit $13_1$. During said introduction, the third portion 26 of the adapter housing $12_1$ is centered by way of the conical transition region 78 such that the third portion 26 is guided into the pilot bore 28. The end-face wall 68 comprises a smooth, planar surface such that an optimum connection without any dead volumes and optimum sealing are provided.

The adapter housing $12_1$ is screwed into the internal thread 22 of the receiving opening 24 until the sealing element 44 touches the end-face wall 68 of the pilot bore 28 by way of the first sealing portion 48. Particularly good sealing can be produced as a result of the first sealing portion 48, which projects forward from the adapter housing, when the adapter housing is moved forward, being acted upon with an axial compressive force which results in elastic or plastic deforming of said sealing portion also in the radial direction. The seal then fits snugly to the end face 68 or the wall 66 completely filling out any dead spaces possibly existing and providing a complete seal.

Once the adapter housing $12_1$ is screwed into the socket unit $13_1$, a capillary tube 38, for example, can now be connected to the adapter housing $12_1$, which is shown in FIG. 2. In the example shown, the connector housing 36 comprises an external thread 72 which can be screwed into the internal thread 34 of the connecting portion 32 of the bore 14 of the adapter housing $12_1$. The capillary tube 38 projects axially beyond the connector housing 36. An intermediate piece 74, which comprises an outside diameter which corresponds substantially to the second inside diameter of the bore 14, is pushed onto the projecting portion of the capillary tube 38. The capillary tube 38 is sealed in relation to the adapter housing $12_1$ by means of a further sealing element 76 and, in this case, abuts against an end face 80 of the closure 64.

The capillary tube 38 is consequently connected to the closure 64 butt to butt. The further sealing element 76 seals the capillary tube 38 both at the end face 52 of the closure 64 and in relation to the bore 14 such that, here too, no dead spaces worth mentioning can be created. Sealing is effected in an analogous manner to that in the pilot bore 28 by the sealing element 76 being caused to deform elastically or plastically as a result of pressure being applied by means of the intermediate piece 74 in order to fill and to seal sealing gaps in a complete manner. Using conveying devices which are not shown, the fluid to be analyzed is conveyed from behind through the capillary tube 38, the closure 64, the pre-column 56, the through-bore 50 and the socket capillary 70.

It is also possible, however, to connect differently constructed connector housings to the adapter housing $12_1$. In addition, the closure 64 could be omitted and its function taken over possibly by the intermediate piece 74. The closure 64 could also be connected fixedly to the adapter housing 12 as a rear stop or could even be realized in one piece with said adapter housing. The third sealing portion 49 could then be expanded during assembly, for example by means of a conical stop face of the closure 64, and clamped firmly in place.

Figure 3:
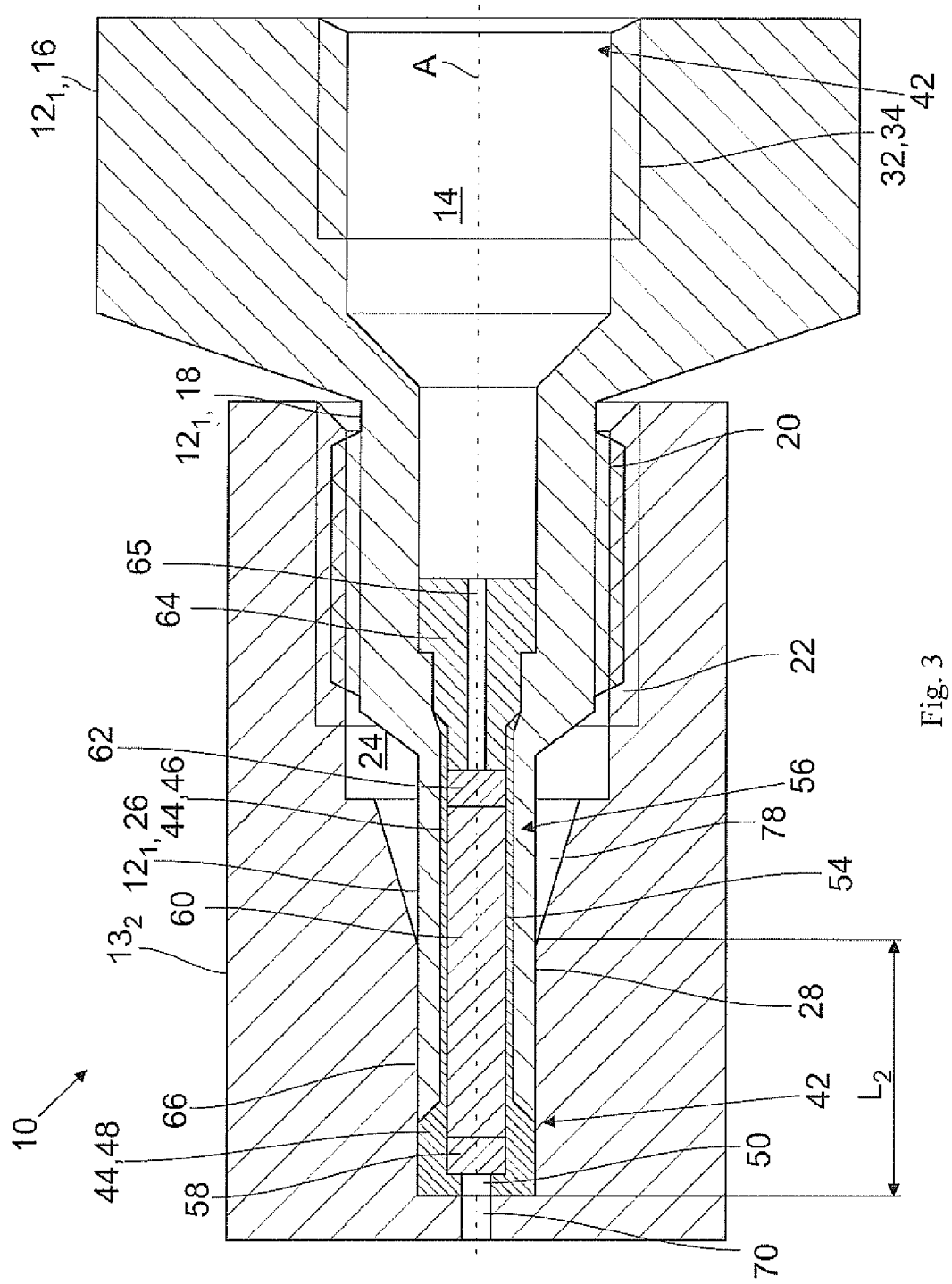
FIG. 3 shows the connecting device according to FIG. 1, wherein the adapter housing is screwed into a second socket unit with a pilot bore length which is longer than that of the first socket unit.

In FIG. 3, the adapter housing $12_1$ shown in FIGS. 1 and 2 is screwed into a second socket unit $13_2$ which comprises a pilot bore 28 with a greater length $L_2$ compared to the first socket unit $13_1$ which is shown in FIGS. 1 and 2. It can be seen that the adapter housing $12_1$ can be introduced without modification into pilot bores with different lengths. The single pre-requisite is that the second portion 18 of the adapter housing $12_1$ is long enough, which is able to be met, however, without a great deal of expenditure. Said flexibility is essentially achieved as a result of the sealing element 44 sealing the end-face wall 68 of the pilot bore 28 in an axial manner such that the necessary surface pressure is determined by how far the adapter housing $12_1$ is screwed into the socket unit 13.

Figure 4:
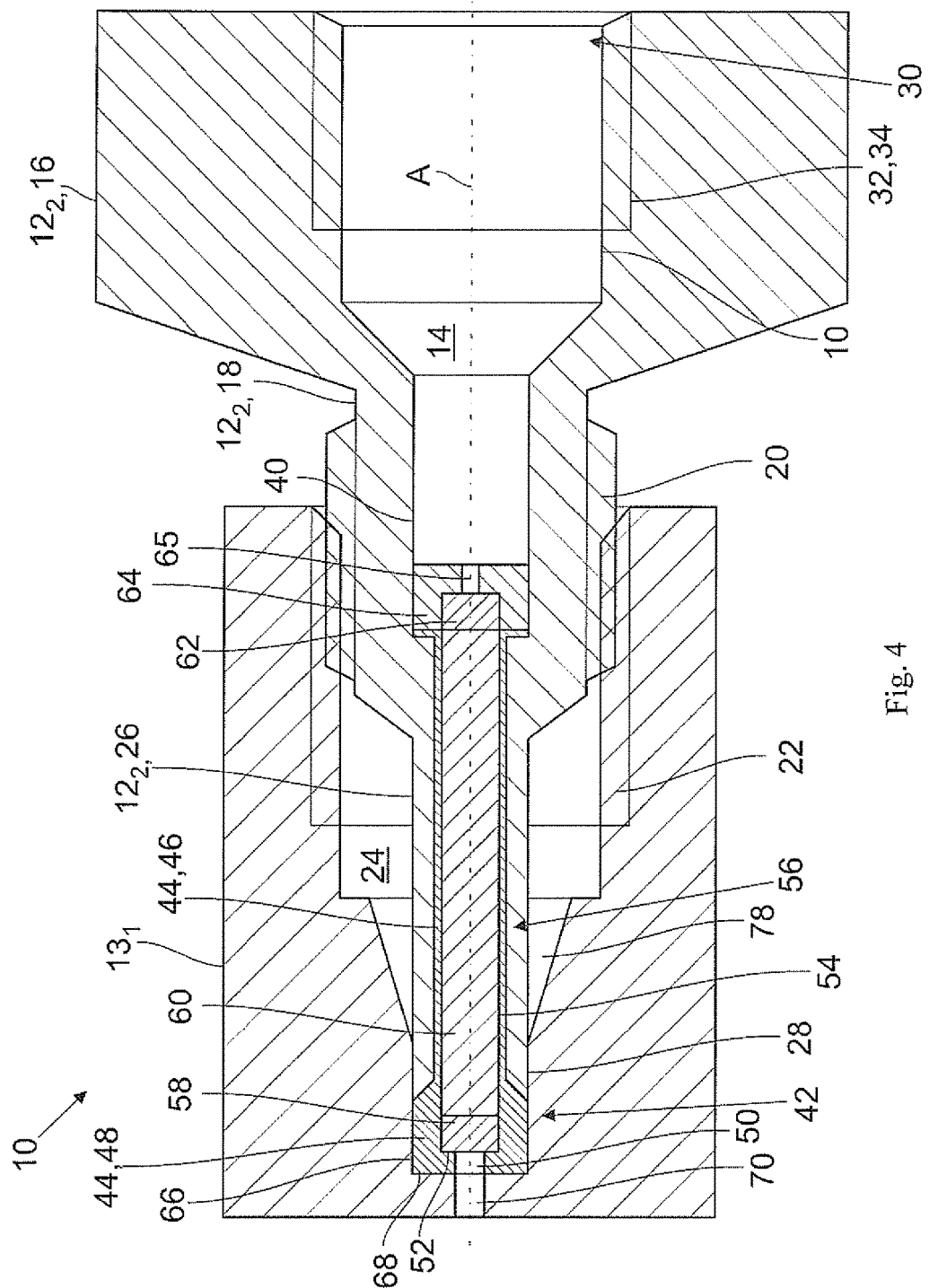
FIG. 4 shows a connecting device with a second embodiment of the adapter housing according to the invention.

FIG. 4 shows a second exemplary embodiment of the adapter housing $12_2$ according to the invention. It differs substantially from the first exemplary embodiment in that the further filter 62 is incorporated in the closure 64 and that the bore 14 only comprises three diameters which all merge into one another in a step-shaped manner. As a result, the sealing element 44 is not pressed against a conical transition, but against a step-shaped transition and is fixed in its position.

LIST OF REFERENCES

10 Connecting device
12, $12_1$, $12_2$ Adapter housing
13, $13_1$, $13_2$ Socket unit
14 Bore
16 First portion
18 Second portion
20 External thread
22 Internal thread
24 Receiving opening
26 Third portion
28 Pilot bore
30 First opening
32 Connecting portion
34 Internal thread
36 Connector housing
38 Capillary tube
40 Fitting portion
42 Second opening
44 Sealing element
46 Second sealing portion
48 First sealing portion
49 Third sealing portion
50 Through-bore
52 End face
54 Sleeve
56 Pre-column
58 Filter
60 Pre-column packing
62 Further filter
64 Closure
65 Through-channel
66 Radial wall
68 End-face wall
70 Socket capillary tube
72 External thread
74 Intermediate piece
76 Further sealing element
78 Conical transition portion
80 End face
A Longitudinal axis
P Arrow

What is claimed is:

1. An adapter housing for receiving a component and configured to be releasably connected to a socket unit, wherein the socket unit comprises: a receiving opening; a pilot bore axially connected to the receiving opening, the pilot bore having a radial wall and an end-face wall, and a socket capillary tube axially connected to the end-face wall, the socket capillary tube configured to direct a fluid to be analyzed, the adapter housing configured to be introduced into the receiving opening, the adapter housing comprises:
 a connecting portion configured to be releasably fastened to a connector housing to supply the fluid directed through the connector housing;
 a pre-column arranged in a bore of the adapter housing, where the bore passes through the adapter housing, the pre-column including a packing material,
 a sealing element is connected to the adapter housing and seals the adapter housing in relation to the socket unit on the radial wall and on the end-face wall when the adapter housing is introduced into the receiving opening of the socket unit, the sealing element surrounds a lateral surface of the pre-column and along an entire length of the pre-column so that the fluid does not come into contact with a material of the adapter housing whilst the fluid flows through the pre-column,
 in that the sealing element comprises a first sealing portion, a second sealing portion and a third sealing portion, the first sealing portion configured to seal the adapter housing in relation to the socket unit, the second sealing portion surrounding the lateral surface of the pre-column, and the third sealing portion having a radially widened region in relation to the second sealing portion, the third sealing portion is pressed directly or indirectly by a closure against a stop region of the adapter housing for the rearward sealing of the pre-column or for fixing the sealing element.

2. The connecting device of claim 1, in that the third sealing portion is pressed directly or indirectly by a closure against a stop region of the adapter housing for fixing the sealing element.

3. The connecting device of claim 1, in that the pre-column comprises a filter for filtering the fluid to be analyzed and for restraining the pre-column packing material.

4. The connecting device of claim 3, in that the sealing element comprises a through-bore extending coaxially with respect to the socket capillary tube, the through-bore having a smaller diameter than an inner diameter of the second sealing portion to create an end face.

5. The connecting device of claim 4, in that the filter abuts against an end face of the sealing element in a mounted state.

6. The connecting device of claim 1, wherein the closure comprises a central through—channel for directing the fluid to be analyzed to the pre-column.

7. The connecting device of claim 3, in that the pre-column further comprises a further filter for filtering the fluid to be analyzed and for restraining the pre-column packing, in that the further filter abuts against the closure in the mounted state.

8. The connecting device of claim 7, in that the further filter is incorporated in the closure.

9. The connecting device of claim 1, in that the sealing element is bio-inert along an entire length of the pre-column.

10. The connecting device of claim 1, in that the sealing element is polyetheretherketone.

11. The connecting device of claim 1, in that the sealing element touches the end-face wall of the pilot bore by way of the first sealing portion.

12. The connecting device of claim 1, further comprising a sleeve arranged between an outside of the sealing element and an inner wall of the pilot bore.

13. The connecting device of claim 1, in that the sealing element is deformed elastically or plastically when the adapter housing is mounted in the socket unit.

\* \* \* \* \*